US009131651B2

(12) United States Patent
Cayley et al.

(10) Patent No.: US 9,131,651 B2
(45) Date of Patent: Sep. 15, 2015

(54) CE43-67B INSECTICIDAL COTTON

(75) Inventors: Patricia Jane Cayley, Bracknell (GB); David Vincent Negrotto, Research Triangle Park, NC (US); Jason Barnett, Gaithersburg, MD (US)

(73) Assignee: Syngenta Participants AG, Basel (CH)

( * ) Notice: Subject to any disclaimer, the term of this patent is extended or adjusted under 35 U.S.C. 154(b) by 1379 days.

(21) Appl. No.: 12/900,013

(22) Filed: Oct. 7, 2010

(65) Prior Publication Data

US 2011/0020828 A1 Jan. 27, 2011

Related U.S. Application Data

(62) Division of application No. 11/915,862, filed as application No. PCT/EP2006/004546 on May 15, 2006, now Pat. No. 7,834,254.

(60) Provisional application No. 60/755,941, filed on Jan. 3, 2006, provisional application No. 60/686,869, filed on Jun. 2, 2005.

(51) Int. Cl.

| | |
|---|---|
| ***C12Q 1/68*** | (2006.01) |
| ***A01H 5/10*** | (2006.01) |
| ***C12N 15/82*** | (2006.01) |

(52) U.S. Cl.

CPC .............. *A01H 5/10* (2013.01); *C12N 15/8286* (2013.01)

(58) Field of Classification Search

USPC ................................ 435/6.12, 91.2; 536/24.3

See application file for complete search history.

(56) References Cited

U.S. PATENT DOCUMENTS

| | | | |
|---|---|---|---|
| 6,740,488 | B2 | 5/2004 | Rangwala et al. |
| 2004/0148666 | A1 | 7/2004 | Rangwala et al. |

FOREIGN PATENT DOCUMENTS

| | | |
|---|---|---|
| WO | 93/07278 | 4/1993 |
| WO | 01/45122 | 6/2001 |
| WO | 02/15701 | 2/2002 |
| WO | 02/40677 | 5/2002 |

OTHER PUBLICATIONS

Feng et al. 2006, J. Integrative Plant Biol. 46:5-14.
Xu et al. 2008, BMC Genomics 9:108.

*Primary Examiner* — Kenneth R. Horlick
*Assistant Examiner* — Joyce Tung
(74) *Attorney, Agent, or Firm* — Yoshimi D. Barron

(57) ABSTRACT

The present application relates an insect resistant transgenic cotton plant. In particular, it relates to a specific event, designated CE43-67B. The application also relates to polynucleotides which are characteristic of the CE43-67B event, plants comprising said polynucleotides, and methods of detecting the CE43-67B event.

14 Claims, No Drawings

SEQUENCE LISTING

```
<160> NUMBER OF SEQ ID NOS: 19

<210> SEQ ID NO 1
<211> LENGTH: 545
<212> TYPE: DNA
<213> ORGANISM: Artificial sequence
<220> FEATURE:
<223> OTHER INFORMATION: CE43-67B nucleotide motif

<400> SEQUENCE: 1

attcattaga gccttctaca agttgaagga agagctagtt cgagcttttg gttttctgtg     60

aaagttgata ttttgttagt gttttggaat cactgctcgt agatgattca tggtgtaatt    120

gggaatttag atgtagccta aacccctact ctatattctc aaagtaagtg ttcttatgcc    180

tatgattaaa tgtgatatat gtatgcttgt gaaattatga aattatgagc atatatgaga    240

tgctatgaca tatgctataa gcatttgata acttggacaa cttaataaca cattgcggat    300

acggccatgc tggccgcccg ggcaccggta aatttcctgc agggctagca gatctctcga    360

ggtttaaacg ggcccacgcg tgcggccgct ccggattcga attaattaac gtacgaagct    420

tgcatgcctg caggtcgaca aaatttagaa cgaacttaat tatgatctca aatacattga    480

tacatatctc atctagatct aggttatcat tatgtaagaa agttttgacg aatatggcac    540

gacaa                                                                545


<210> SEQ ID NO 2
<211> LENGTH: 1198
<212> TYPE: DNA
<213> ORGANISM: Artificial sequence
<220> FEATURE:
<223> OTHER INFORMATION: CE43-67B nucleotide motif

<400> SEQUENCE: 2

ttgcggttct gtcagttcca aacgtaaaac ggcttgtccc gcgtcatcgg cgggggtcat     60

aacgtgactc ccttaattct ccgctcatga tcagattgtc gtttcccgcc ttcagtttaa    120

actatcagtg tttataatgt gctaatgatg tgaatatgca gtgcttatgt gcggaaaatc    180

aataagtaaa tatgtgataa caatgtggat attttggcct tgtgctatta tgagaccgtt    240

ggatatagtt ggcatgccat agggttgtga gtactcatct ttgtgatgtt gtttatgggg    300

cgttggggcc caaggacaat ttttggaaag ataagggaat gtgagctaag cttaattcac    360
```

-continued

```
cgggatatgt gtgtttggtg tgctggagag tgttaactat atgcttcact tatgggacat    420

gtacgacact atgagtcaat attggtctgt tggtgatcca tgtattcgat gtgtggtgat    480

agggtccaca ttatatttca tatcctcaag agccaaacta tcataaaaca tgactgaaag    540

tgactaaatg tgattaaaat gtgttgtagt atatgcttaa atattcatgt gattaatgtg    600

taaatattca tgaaagatga taaaatgtgt taaacatgac ataggagtag aagatgttat    660

gattatattg catgtttgct ttgttgatgc ataatgattt gtttgcgtag tggttgtttt    720

caccattcac tgagcttgtt aagctcacgc actccttttt aatcattaca gataattagt    780

gccggtgtga gtggtatggt ctcgaggggt gatccaagcc agacatttag ttgctattag    840

taggtgtttt ttctattatt tgtgtttttg agactttaag gcaatgtggt agactttata    900

tcagctttgt taagttattt tggggctatt tgcatgttat ttacgtttgg aagcttgtag    960

attttgaata tgatattttg attgttgttt ggttattcag aagcttattt atctaggtga   1020

ataaatcatg ttatttaggg atgagtttaa atgatctaat tgttgatata tgctaaaatt   1080

tggtagtttg gagcaaggta ttgataatag gattactaaa atgatatcga aagtgcagca   1140

aaacagaata tagaattgtt attgatacct tggcccgagt atcaatactc gaggtaaa     1198


<210> SEQ ID NO 3
<211> LENGTH: 30
<212> TYPE: DNA
<213> ORGANISM: Artificial sequence
<220> FEATURE:
<223> OTHER INFORMATION: CE43-67B nucleotide motif

<400> SEQUENCE: 3

gcatttgata acttggacaa cttaataaca                                      30


<210> SEQ ID NO 4
<211> LENGTH: 30
<212> TYPE: DNA
<213> ORGANISM: Artificial sequence
<220> FEATURE:
<223> OTHER INFORMATION: CE43-67B nucleotide motif

<400> SEQUENCE: 4

aaactatcag tgtttataat gtgctaatga                                      30


<210> SEQ ID NO 5
<211> LENGTH: 21
<212> TYPE: DNA
<213> ORGANISM: Artificial sequence
<220> FEATURE:
<223> OTHER INFORMATION: CE43-67B nucleotide motif

<400> SEQUENCE: 5

ttctcctgca gcctctgatt c                                               21


<210> SEQ ID NO 6
<211> LENGTH: 21
<212> TYPE: DNA
<213> ORGANISM: Artificial sequence
<220> FEATURE:
<223> OTHER INFORMATION: CE43-67B nucleotide motif

<400> SEQUENCE: 6

tgtcgtgcca tattcgtcaa a                                               21


<210> SEQ ID NO 7
<211> LENGTH: 3546
```

<212> TYPE: DNA
<213> ORGANISM: Artificial sequence
<220> FEATURE:
<223> OTHER INFORMATION: CE43-67B nucleotide motif

<400> SEQUENCE: 7

```
atggacaaca accccaacat caacgagtgc atcccctaca actgcctgag caaccccgag     60

gtggaggtgc tgggcggcga gcgcatcgag accggctaca cccccatcga catcagcctg    120

agcctgaccc agttcctgct gagcgagttc gtgcccggcg ccggcttcgt gctgggcctg    180

gtggacatca tctggggcat cttcggcccc agccagtggg acgccttcct ggtgcagatc    240

gagcagttga taaaccaacg catagaggaa ttcgcccgca accaggccat cagccgcctg    300

gagggcctga gcaacctgta ccaaatctac gccgagagct tccgcgagtg ggaggccgac    360

cccaccaacc ccgccctgcg cgaggagatg cgcatccagt tcaacgacat gaacagcgcc    420

ctgaccaccg ccatccccct gttcgccgtg cagaactacc aggtgcccct gctgagcgtg    480

tacgtgcagg ccgccaacct gcacctgagc gtgctgcgcg acgtcagcgt gttcggccag    540

cgctggggct tcgacgccgc caccatcaac agccgctaca acgacctgac ccgcctgatc    600

ggcaactaca ccgaccacgc cgtgcgctgg tacaacaccg gcctggagcg cgtgtggggt    660

cccgacagcc gcgactggat caggtacaac cagttccgcc gcgagctgac cctgaccgtg    720

ctggacatcg tgagcctgtt ccccaactac gacagccgca cctaccccat ccgcaccgtg    780

agccagctga cccgcgagat ttacaccaac cccgtgctgg agaacttcga cggcagcttc    840

cgcggcagcg cccagggcat cgagggcagc atccgcagcc cccacctgat ggacatcctg    900

aacagcatca ccatctacac cgacgcccac cgcggcgagt actactggag cggccaccag    960

atcatggcca gccccgtcgg cttcagcggc cccgagttca ccttcccccct gtacggcacc   1020

atgggcaacg ctgcacctca gcagcgcatc gtggcacagc tgggccaggg agtgtaccgc   1080

accctgagca gcaccctgta ccgtcgacct ttcaacatcg gcatcaacaa ccagcagctg   1140

agcgtgctgg acggcaccga gttcgcctac ggcaccagca gcaacctgcc cagcgccgtg   1200

taccgcaaga gcggcaccgt ggacagcctg gacgagatcc cccctcagaa caacaacgtg   1260

ccacctcgac agggcttcag ccaccgtctg agccacgtga gcatgttccg cagtggcttc   1320

agcaacagca gcgtgagcat catccgtgca cctatgttca gctggattca ccgcagtgcc   1380

gagttcaaca acatcatccc cagcagccag atcacccaga tcccccctgac caagagcacc   1440

aacctgggca gcggcaccag cgtggtgaag ggccccggct tcaccggcgg cgacatcctg   1500

cgccgcacca gccccggcca gatcagcacc ctgcgcgtga acatcaccgc cccccctgagc   1560

cagcgctacc gcgtccgcat ccgctacgcc agcaccacca acctgcagtt ccacaccagc   1620

atcgacggcc gccccatcaa ccagggcaac ttcagcgcca ccatgagcag cggcagcaac   1680

ctgcagagcg gcagcttccg caccgtgggc ttcaccaccc ccttcaactt cagcaacggc   1740

agcagcgtgt tcaccctgag cgcccacgtg ttcaacagcg gcaacgaggt gtacatcgac   1800

cgcatcgagt tcgtgcccgc cgaggtgacc ttcgaggccg agtacgacct ggagagggct   1860

cagaaggccg tgaacgagct gttcaccagc agcaaccaga tcggcctgaa gaccgacgtg   1920

accgactacc acatcgacca ggtgagcaac ctggtggagt gcttaagcga cgagttctgc   1980

ctggacgaga agaaggagct gagcgagaag gtgaagcacg ccaagcgcct gagcgacgag   2040

cgcaacctgc tgcaggaccc caacttccgc ggcatcaacc gccagctgga ccgcggctgg   2100

cgaggcagca ccgatatcac catccagggc ggcgacgacg tgttcaagga gaactacgtg   2160
```

```
accctgctgg gcaccttcga cgagtgctac cccacctacc tgtaccagaa gatcgacgag   2220

agcaagctga aggcctacac ccgctaccag ctgcgcggct acatcgagga cagccaggac   2280

ctggaaatct acctgatccg ctacaacgcg aagcacgaga ccgtgaacgt gcccggcacc   2340

ggcagcctgt ggcccctgag cgcccccagc cccatcggca agtgcgggga gccgaatcga   2400

tgcgctccgc acctggagtg gaacccggac ctagactgca gctgcaggga cggggagaag   2460

tgcgcccacc acagccacca cttcagcctg gacatcgacg tgggctgcac cgacctgaac   2520

gaggacctgg gcgtgtgggt gatcttcaag atcaagaccc aggacggcca cgcccgcctg   2580

ggcaatctag agttcctgga ggagaagccc ctggtgggcg aggccctggc ccgcgtgaag   2640

cgtgctgaga agaagtggcg cgacaagcgc gagaagctgg agtgggagac caacatcgtg   2700

tacaaggagg ccaaggagag cgtggacgcc ctgttcgtga acagccagta cgaccgcctg   2760

caggccgaca ccaacatcgc catgatccac gccgccgaca agcgcgtgca cagcattcgc   2820

gaggcctacc tgcccgagct gagcgtgatc cccggtgtga acgccgccat cttcgaggaa   2880

ctcgagggcc gcatcttcac cgccttcagc ctgtacgacg cccgcaacgt gatcaagaac   2940

ggcgacttca acaacggcct gagctgctgg aacgtgaagg gccacgtgga cgtggaggag   3000

cagaacaacc accgcagcgt gctggtggtg cccgagtggg aggccgaggt gagccaggag   3060

gtgcgcgtgt gccccggccg cggctacatc ctgcgcgtga ccgcctacaa ggagggctac   3120

ggcgagggct gcgtgaccat ccacgagatc gagaacaaca ccgacgaact caagttcagc   3180

aactgcgtgg aggaggaggt ttaccccaac aacaccgtga cctgcaacga ctacaccgcg   3240

acccaggagg agtacgaagg cacctacacc tctcgcaaca ggggttacga cggcgcctac   3300

gagtccaaca gctccgtgcc agctgactac gccagcgcct acgaggagaa agcctacacc   3360

gacggtagac gcgacaaccc atgtgagagc aacagaggct acggcgacta cacccccctg   3420

cccgctggat acgtgaccaa ggagctggag tacttccccg agaccgacaa ggtgtggatc   3480

gagattggcg agaccgaggg caccttcatc gtggacagcg tggagctgct gctgatggag   3540

gagtag                                                              3546
```

<210> SEQ ID NO 8
<211> LENGTH: 21
<212> TYPE: DNA
<213> ORGANISM: Artificial sequence
<220> FEATURE:
<223> OTHER INFORMATION: CE43-67B nucleotide motif

<400> SEQUENCE: 8

```
ccctcgagac cataccactc a                                               21
```

<210> SEQ ID NO 9
<211> LENGTH: 21
<212> TYPE: DNA
<213> ORGANISM: Artificial sequence
<220> FEATURE:
<223> OTHER INFORMATION: CE43-67B nucleotide motif

<400> SEQUENCE: 9

```
ccctcgagac cataccactc a                                               21
```

<210> SEQ ID NO 10
<211> LENGTH: 22
<212> TYPE: DNA
<213> ORGANISM: Artificial sequence
<220> FEATURE:
<223> OTHER INFORMATION: CE43-67B nucleotide motif

<400> SEQUENCE: 10
gcggttctgt cagttccaaa cg 22

<210> SEQ ID NO 11
<211> LENGTH: 23
<212> TYPE: DNA
<213> ORGANISM: Artificial sequence
<220> FEATURE:
<223> OTHER INFORMATION: CE43-67B nucleotide motif

<400> SEQUENCE: 11
gttcgagctt ttggttttct gtg 23

<210> SEQ ID NO 12
<211> LENGTH: 24
<212> TYPE: DNA
<213> ORGANISM: Artificial sequence
<220> FEATURE:
<223> OTHER INFORMATION: CE43-67B nucleotide motif

<400> SEQUENCE: 12
ccgtatccgc aatgtgttat taag 24

<210> SEQ ID NO 13
<211> LENGTH: 21
<212> TYPE: DNA
<213> ORGANISM: Artificial sequence
<220> FEATURE:
<223> OTHER INFORMATION: CE43-67B nucleotide motif

<400> SEQUENCE: 13
ccctcgagac cataccactc a 21

<210> SEQ ID NO 14
<211> LENGTH: 22
<212> TYPE: DNA
<213> ORGANISM: Artificial sequence
<220> FEATURE:
<223> OTHER INFORMATION: CE43-67B nucleotide motif

<400> SEQUENCE: 14
ctcccttaat tctccgctca tg 22

<210> SEQ ID NO 15
<211> LENGTH: 29
<212> TYPE: DNA
<213> ORGANISM: Artificial sequence
<220> FEATURE:
<223> OTHER INFORMATION: CE43-67B nucleotide motif

<400> SEQUENCE: 15
tcacatcatt agcacattat aaacactga 29

<210> SEQ ID NO 16
<211> LENGTH: 26
<212> TYPE: DNA
<213> ORGANISM: Artificial sequence
<220> FEATURE:
<223> OTHER INFORMATION: CE43-67B nucleotide motif
<220> FEATURE:
<221> NAME/KEY: misc_feature
<222> LOCATION: (1)..(1)
<223> OTHER INFORMATION: FAM label at 5' end
<220> FEATURE:
<221> NAME/KEY: misc_feature
<222> LOCATION: (26)..(26)

-continued

<223> OTHER INFORMATION: TEMRA label at 3' end

<400> SEQUENCE: 16
tcagattgtc gtttcccgcc ttcagt 26

<210> SEQ ID NO 17
<211> LENGTH: 27
<212> TYPE: DNA
<213> ORGANISM: Artificial sequence
<220> FEATURE:
<223> OTHER INFORMATION: CE43-67B nucleotide motif

<400> SEQUENCE: 17
tgcttgtgaa attatgaaat tatgagc 27

<210> SEQ ID NO 18
<211> LENGTH: 33
<212> TYPE: DNA
<213> ORGANISM: Artificial sequence
<220> FEATURE:
<223> OTHER INFORMATION: CE43-67B nucleotide motif

<400> SEQUENCE: 18
taacataatg acatatttat tttcacatca gtt 33

<210> SEQ ID NO 19
<211> LENGTH: 23
<212> TYPE: DNA
<213> ORGANISM: Artificial sequence
<220> FEATURE:
<223> OTHER INFORMATION: CE43-67B nucleotide motif
<220> FEATURE:
<221> NAME/KEY: misc_feature
<222> LOCATION: (1)..(1)
<223> OTHER INFORMATION: TET label at 5' end
<220> FEATURE:
<221> NAME/KEY: misc_feature
<222> LOCATION: (23)..(23)
<223> OTHER INFORMATION: TEMRA label at 3' end

<400> SEQUENCE: 19
tatatgagat gctatgacat atg 23

CE43-67B INSECTICIDAL COTTON

This application is a divisional of U.S. patent application Ser. No. 11/915,862, filed May 19, 2008, which is a National Stage Entry of PCT/EP06/04546, filed May 15, 2006, which claims the benefit of U.S. Provisional Application No. 60/755,941, filed Jan. 3, 2006, and U.S. Provisional Application No. 60/686,869, filed Jun. 2, 2005, all of which are incorporated by reference herein in their entirety.

The present invention relates to inter alia, polynucleotides and methods of use thereof and in particular to cotton plants comprising said polynucleotides. Specifically, the invention relates to a cotton event designated CE43-67B which comprises a Cry1Ab gene. The invention also relates to methods of identifying specific cotton events which contain a gene capable of conferring insect resistance on said cotton plants.

Plant pests are a major factor in the loss of the world's important agricultural crops. About $8 billion is lost every year in the U.S. due to infestations of plants by non-mammalian pests including insects. In addition to losses in field crops, insect pests are also a burden to vegetable and fruit growers, to producers of ornamental flowers, and to home gardeners.

Insect pests are mainly controlled by intensive applications of chemical pesticides, which are active through inhibition of insect growth, prevention of insect feeding or reproduction, or cause death. Good control of insect pests can thus be reached, but these chemicals can sometimes also affect other, beneficial insects. Another problem resulting from the wide use of chemical pesticides is the appearance of resistant insect varieties. This has been partially alleviated by various resistance management practices, but there is an increasing need for alternative pest control agents. Biological pest control agents, such as *Bacillus thuringiensis* strains expressing pesticidal toxins like δ-endotoxins, have also been applied to crop plants with satisfactory results, offering an alternative or compliment to chemical pesticides. The genes coding for some of these δ-endotoxins have been isolated and their expression in heterologous hosts has been shown to provide another tool for the control of economically important insect pests. In particular, the expression of the insecticidal toxin Cry1Ac from *Bacillus thuringiensis* in transgenic plants, has provided efficient protection against selected insect pests, and transgenic plants expressing this toxin have been commercialised, allowing farmers to reduce applications of chemical insect control agents. Cry1Ac is one of a large family of insecticidal toxins produced by different strains of *Bacillus thuringiensis*. Each toxin in the family has a unique spectrum of insecticidal activity.

The cotton family, genus *Gossypium*, a member of the Malvaceae, consists of 39 species, of which *Gossypium hirsutum* is the most commonly cultivated species. Three other species are also cultivated: *G. arboreum, G. barbadense*, and *G. herbaceum*. These cultivated species are grown primarily for the seed hairs that are made into textiles. Cotton is suitable as a textile fibre because the mature dry hairs twist in such a way that fine strong threads can be spun from them. Other products, such as cottonseed oil, cake, and cotton linters are by-products of fibre production.

Damage to cotton crops by insect pests throughout the world results in a significant yield loss each year. Effective control of these pests to minimise yield loss is of great economic importance. Examples of insect pests of cotton include Beet armyworm (*Spodoptera exigua*), Boll weevil (*Anthonomus grandis grandis*), Cabbage looper (*Thichoplusia ni*), Clouded plant bug (*Neurocolpus nubilus*), Cotton aphid (*Aphis gossypii*), Cotton bollworm (*Heliocoverpa zea*), Cutworms (*Feltia subterranea, Peridroma saucia, Agrotis ipsilon*), European corn borer (*Ostrinia nubilalis*), Fall armyworm (*Spodoptera frugiperda*), Pink boll worm (*Pectinophera gossypiella*), Seedling thrips (*Frankliniella* spp.), Soybean looper (*Pseudoplusia includens*), Stink bugs (*Nezara viridula, Acrosternum hilare, Euschistus servos*), Tarnished plant bug (*Lygus lineolaris*), Tobacco budworm (*Heliothis virescens*) and Whiteflies (*Trialeurodes abutilonea, Bemisia tabaci*).

Transformation and regeneration of cotton plants is now a well-established procedure, typically based on *Agrobacterium tumefaciens* mediated transfer of foreign DNA into cotton plant parts and regeneration of said plant parts in tissue culture into fully fertile, transgenic cotton plants.

There exists a requirement to generate a new cotton plant that is insect resistant so that yield loss through damage to cotton crops by insect pests is reduced. An insect resistant cotton plant could reduce the need to apply chemical pesticides, which may be detrimental to other, beneficial insects and the environment. In particular, it is desirable to provide an alternative insect resistant plant to transgenic plants comprising the Cry1Ac gene from *Bacillus thuringiensis.*

The present invention provides, inter alia, a specific cotton event (referred to hereinafter as "CE43-67B") and methods for the identification thereof. This specific event has been selected based on, inter alia, its agronomic performance, efficacy and molecular characteristics. It is believed that the characteristics of this event are far superior to like transformants based upon, inter alia, the integration site of the transgene during the transformation process.

"CE43-67B event" in the context of this application refers to the original insecticidal transgenic cotton plant described herein and any plant material derived therefrom, including seeds. "Insecticidal" as used herein refers to any inhibitory effect on an insect, including but not limited to reduced feeding, retarded growth, reduced fecundity, paralysis or death. "Fecundity" comprises all aspects related to reproduction such as reproductive ability, reproductive frequency and number of offspring. Also embraced by this invention is any plant material derived from the CE43-67B event, including seeds.

The CE43-67B event exhibits a novel genotype comprising at least one expression cassette. The cassette comprises a suitable promoter for expression in plants operably linked to a gene that encodes a Cry1Ab insecticidal toxin, useful in controlling a wide spectrum of lepidopteran insect pests, and a suitable polyadenylation signal. Suitable promoters may be isolated from, inter alia, plants. Numerous plant promoters have been isolated and characterised including constitutive, switchable and/or tissue specific promoters. Suitable promoters may be selected from the following, non-limiting group: CaMV35S, FMV35S, Ubiquitin, Act2, NOS, OCS, Cestrum yellow leaf curl virus promoter, Patatin, E9, alcA/alcR switch, GST switch, RMS switch, oleosin, Gelvin, ribulose bisphosphate carboxylase-oxygenase small sub-unit, actin 7, MR7 promoter (maize), Gos 9 (rice), GOS2 promoters, MasOcs (or super promoter), RolD promoter (*Agrobacterium rhizogenes*), SuperMAS promoter, and Suc2 promoter (*Arabidopsis*). In one embodiment of the present invention, the promoter is the Actin promoter, ACT2, from *Arabidopsis thaliana*. Additional elements such as enhancer sequences may also be incorporated into the expression cassette in order to boost levels of gene expression, for example transcriptional or translational enhancers, such as tobacco etch virus (TEV) translation activator, CaMV35S enhancer, and FMV35S enhancer. Alternatively it may be desirable to include a targeting sequence, for example, to direct transportation of the Cry1Ab toxin to a particular cellular compartment. For example, if it is desired to provide the protein outside of the cell then an extracellular targeting sequence may be ligated to the polynucleotide encoding the Cry1Ab protein. Other examples of targeting include targeting to a specific intracellular organelle or compartment, for example to the endoplasmic reticulum using a 'KDEL' retention sequence. Numerous polyadenylation signals have been isolated and characterised. Examples of suitable polyadenylation signals functional in plants include that from the nopaline synthase gene (nos) of *Agrobacterium tumefaciens*, from the proteinase inhibitor II gene and from the alpha-tubulin gene (EP-A 652,286). In one embodiment of the present invention, the polyadenylation signal is that from the nos gene of *Agrobacterium tumefaciens*.

The polynucleotide encoding the Cry1Ab protein may be codon-optimised or otherwise altered to enhance for example, translation once it is incorporated into plant material. Such codon optimisation may also be used to alter the predicted secondary structure of the RNA transcript produced in any transformed cell, or to destroy cryptic RNA instability elements present in the unaltered transcript, thereby increasing the stability and/or availability of the transcript in the transformed cell (Abler and Green (1996) Plant Molecular Biology (32) pp. 63-78). Codon optimisation may also be employed to alter a heterologous DNA coding sequence so that it more closely resembles the coding sequence of a gene of the host. For example, a bacterial gene can be codon optimised to increase the ratio of cytosine and guanine bases to adenine and thymine bases so that it more closely resembles a plant (e.g. cotton or maize) gene, yet encodes the same protein. Such codon optimisation may be performed in accordance with standard codon usage tables.

In a precursor to the CE43-67B event, a second cassette is present that comprises a gene which, when expressed, can be used as a selectable marker. Numerous selectable markers have been characterised, including some that confer tolerance to antibiotics and others that confer tolerance to herbicides. Examples of suitable selectable marker genes include those that confer tolerance to hygromycin, kanamycin or gentamycin. Further suitable selectable markers include genes that confer resistance to herbicides such as glyphosate-based herbicides or resistance to toxins such as eutypine. Other forms of selection are also available such as hormone based selection systems such as the Multi Auto Transformation (MAT) system of Hiroyrasu Ebinuma et al. (1997) PNAS Vol. 94 pp. 2117-2121; visual selection systems which use the known green fluorescence protein, β glucoronidase; and any other selection system such as mannose isomerase (Positech™), xylose isomerase and 2-deoxyglucose (2-DOG). In one embodiment of the present invention, the selectable marker gene is one that confers tolerance to hygromycin. This second expression cassette is useful for selecting transformants during and following plant transformation. Optionally, it may be segregated away from the CE43-67B event precursor after transformation to leave the CE43-67B event itself. The CE43-67B event per se does not comprise a selectable marker cassette. Further expression cassettes are optionally comprised in the CE43-67B event. For example these may provide genes encoding different insecticidal toxins such as VIP3A. Alternatively, these may provide other desirable benefits such as herbicide resistance.

The expression cassettes may be introduced into the plant on the same or different plasmids. If the expression cassettes are present on the same plasmid and introduced into the plant via an *Agrobacterium*-mediated transformation method, they may be present within the same or different T-DNA regions. In one embodiment of the present invention, two expression cassettes are present on different T-DNA regions within different plasmids.

According to the present invention there is provided a polynucleotide which comprises a first region comprising the sequence depicted as SEQ ID NO: 1 and a further region which comprises the sequence depicted as SEQ ID NO: 2.

In a further embodiment said polynucleotide comprises a region which can be amplified by an amplification reaction which reaction uses the primers depicted as SEQ ID NO: 5 and 6.

In a still further embodiment said polynucleotide comprises a still further region which encodes a Cry1Ab gene from *Bacillus thuringiensis*. In a still further embodiment said polynucleotide comprises a region which provides for the *Arabidopsis* actin promoter operably linked to said Cry1Ab gene.

In a further aspect of the invention there is provided a polynucleotide which comprises at least 18 contiguous nucleotides of the sequence depicted as SEQ ID NO: 3. Still further provided is a polynucleotide which comprises at least 20 contiguous nucleotides of the sequence depicted as SEQ ID NO: 3. Still further provided is a polynucleotide which comprises at least 25 contiguous nucleotides of the sequence depicted as SEQ ID NO: 3. Still further provided is a polynucleotide which comprises the sequence depicted as SEQ ID NO: 3.

Still further provided is a polynucleotide which comprises at least 35 contiguous nucleotides of the sequence depicted as nucleotides 246 to 305 of SEQ ID NO: 1. Still further provided is a polynucleotide comprising at least 40 contiguous nucleotides of the sequence depicted as nucleotides 246 to 305 of SEQ ID NO: 1. Still further provided is a polynucleotide comprising at least 50 contiguous nucleotides of the sequence depicted as nucleotides 246 to 305 of SEQ ID NO: 1. Still further provided is a polynucleotide comprising the sequence depicted as nucleotides 246 to 305 of SEQ ID NO: 1.

Still further provided is a polynucleotide comprising at least 50, 100, 150, 200, 300, 400 or 500 contiguous nucleotides of SEQ ID NO: 1, said polynucleotide containing the nucleotide junction between nucleotides 275 and 276 of SEQ ID NO: 1. Still further provided is a polynucleotide which comprises the sequence depicted as SEQ ID NO: 1.

Still further provided is a sequence which is the complement of a sequence described above.

In a further aspect of the invention there is provided is a polynucleotide which comprises at least 18 contiguous nucleotides of the sequence depicted as SEQ ID NO: 4. Still further provided is a polynucleotide which comprises at least 20 contiguous nucleotides of the sequence depicted as SEQ ID NO: 4. Still further provided is a polynucleotide which comprises at least 25 contiguous nucleotides of the sequence depicted as SEQ ID NO: 4. Still further provided is a polynucleotide which comprises the sequence depicted as SEQ ID NO: 4.

Still further provided is a polynucleotide which comprises at least 35 contiguous nucleotides of the sequence depicted as nucleotides 104 to 163 of SEQ ID NO: 2. Still further provided is a polynucleotide which comprises at least 40 contiguous nucleotides of the sequence depicted as nucleotides 104 to 163 of SEQ ID NO: 2. Still further provided is a polynucleotide which comprises at least 50 contiguous nucleotides of the sequence depicted as nucleotides 104 to 163 of SEQ ID NO: 2. Still further provided is a polynucleotide which comprises the sequence depicted as nucleotides 104 to 163 of SEQ ID NO: 2.

Still further provided is a polynucleotide which comprises at least 50, 100, 150, 200, 300, 400 or 500 contiguous nucleotides of SEQ ID NO: 2, said polynucleotide containing the nucleotide junction between nucleotides 133 and 134 or SEQ ID NO: 2. Still further provided is a polynucleotide which comprises the sequence depicted as SEQ ID NO: 2.

Still further provided is a sequence which is the complement of a sequence described above.

In a further embodiment there is provided a cotton plant which comprises a polynucleotide described above. In a still further embodiment there is provided a cotton seed which comprises the polynucleotide as described above. In a further embodiment, said plant is an insecticidal cotton plant which is a precursor to the CE43-67B event, the CE43-67B event per se, or a plant derived therefrom that still comprises a polynucleotide as described above. In a further embodiment said plant comprises a second expression cassette. In one embodiment said second expression cassette encodes a VIP3A insecticidal toxin. In another embodiment, said second expression cassette encodes a protein that provides resistance to a herbicide which comprises glyphosate acid or an agriculturally acceptable salt thereof.

The skilled man is familiar with plant transformation methods. In particular, two principal techniques have been characterised across a wide range of plant species: transformation by *Agrobacterium* and transformation by direct DNA transfer.

*Agrobacterium*-mediated transformation is a commonly used method for transformation of dicotyledonous plants. The foreign DNA to be introduced into the plant is cloned into a binary vector in between left and right border consensus sequences. This is the T-DNA region. The binary vector is transferred into an *Agrobacterium* cell, which is subsequently used to infect plant tissue. The T-DNA region of the vector comprising the foreign DNA is inserted into the plant genome. The marker gene cassette and trait gene cassette may be present on the same T-DNA region, different T-DNA regions in the same vector, or even different T-DNA regions in different vectors. In one embodiment of the present invention, the cassettes are present on different T-DNA regions on different vectors.

Alternatively, direct DNA transfer can be used to introduce the DNA directly into a plant cell. One suitable method of direct transfer may be bombardment of plant cells with a vector comprising the DNA for insertion using a particle gun (particle-mediated biolistic transformation); another established method, 'whiskers', involves coating the DNA onto silicon carbide fibres onto which cells are impaled. Other methods for transforming plant cells include protoplast transformation (optionally in the presence of polyethylene glycols); sonication of plant tissues, cells or protoplasts in a medium comprising the polynucleotide or vector; micro-insertion of the polynucleotide or vector into plant material (optionally employing the known silicon carbide "whiskers" technique), electroporation and the like.

Following transformation, transgenic plants are regenerated from the transformed plant tissue, and progeny possessing the foreign DNA selected using an appropriate marker such as resistance to hygromycin. The skilled man is familiar with the composition of suitable regeneration media. The selectable marker can be segregated away from transgenic events by conventional plant breeding methods, thus resulting in, for example, the CE43-67B event.

A plant of the invention, as described herein, has an insecticidal effect on insects from one or more species from the group comprising *Heliothis* sp. and *Helicoverpa* sp. which may infest it. "Infest" as used herein refers to attack, colonisation, feeding or damage in any way by one or more insects. Thus, for example, the plant of the present invention will provide a self-defence mechanism against infestation by pest insects such as *Helicoverpa zea* (cotton boll worm). As a result, a reduced number of insecticide sprays are required during the cultivation of said plant compared to a non-transgenic cotton plant of the same variety and yield loss through insect pests is kept at a minimal level.

The present invention is not limited to the CE43-67B event itself, but is further extended to include any plant material derived therefrom, including seeds in so far as they contain at least one of the present inventive polynucleotides. The present invention includes, but is not limited to plants that are derived from a breeding cross with the CE43-67B event or a derivative therefrom by conventional breeding or other methods. The invention also includes plant material derived from the CE43-67B event that may comprise additional, modified or fewer polynucleotide sequences compared to the CE43-67B event or exhibit other phenotypic characteristics. For example, it may be desirable to transform plant material derived from the CE43-67B event to generate a new event that possesses an additional trait, such as a second insect resistance gene. This process is known as gene stacking. The second insect resistance gene may encode, for example insecticidal lectins, insecticidal protease inhibitors and insecticidal proteins derived from species of the *Bacillus thuringiensis, Xenorhabdus nematophilus*, or *Photorabdus luminescens*. In one aspect, the second insect resistance gene encodes an insecticidal gene from *Bacillus thuringiensis*. Preferably, the second insect resistance gene encodes a VIP gene from the bacterium *Bacillus thuringiensis*, which VIP gene produces a toxin with a different mode of action or binding site in the insect gut to Cry1Ab for the control of different insect species. The VIP gene may, for example, be VIP3A.

The present invention further provides plant material derived from the CE43-67B event which possesses an additional trait such as herbicide resistance, nematode resistance or fungal resistance. In one embodiment, said additional trait is herbicide resistance. The herbicide resistance trait may be provided, for example, by a herbicide degradation enzyme, or a target-site specific resistant enzyme. In a further embodiment, said herbicide resistance trait provides resistance to a herbicide which comprises glyphosate acid or an agriculturally acceptable salt thereof. In a further embodiment still, said herbicide resistance trait is provided by a gene encoding EPSP synthase or a mutant thereof.

The present invention further provides a method of controlling insects comprising providing the CE43-67B event or plant material derived from the CE43-67B event at a locus where said insects feed. The invention yet further provides a method of controlling insects comprising providing the CE43-67B event or plant material derived from the CE43-67B event at a locus where said insects feed, and applying other agrochemicals to said plant material such as herbicides, fungicides and other insecticidal compounds including other insecticidal proteins. Examples of possible insecticidal compounds include insecticidal lectins, insecticidal protease inhibitors and insecticidal proteins derived from species of the *Bacillus thuringiensis, Xenorhabdus nematophilus*, or *Photorabdus luminescens*. Examples of possible chemicals include pyrethroids, carbamates, imidacloprid, organochlorines, and macromolecules such as spinosad, abamectin or emamectin.

The present invention further provides a method for detecting plant material which is derived from the CE43-67B event, said method comprising: (a) preparing a sample containing the genomic DNA of the plant material to be tested; (b)

obtaining a pair of primers which are suitable for use in an amplification reaction to amplify a sequence selected from the group consisting of: (i) a sequence comprising at least 18 contiguous nucleotides of the sequence depicted as SEQ ID NO: 3 and the complement thereof and (ii) a sequence comprising at least 18 contiguous nucleotides of the sequence depicted as SEQ ID NO: 4 and the complement thereof; (c) adding said pair of primers to said sample and the means for performing an amplification reaction; (d) performing an amplification reaction; and (e) visualising the thus amplified sequence.

There are many amplification methods that may be used in accordance with the methods of the invention. The underlying principle, a known technique to those skilled in the art, is the polymerase chain reaction (PCR). The amplification product from a PCR reaction may be visualised by staining with ethidium bromide and excitation with UV light, typically after size separation using agarose gel electrophoresis. In a particular embodiment of the invention variations of the PCR principle such as TaqMan™ may be used. Such techniques involve labelling at least one of the primers involved in the amplification process with a fluorescent dye. When unbound, the primer adopts a conformation such that no fluorescence can be detected. However, when the primer is bound to a piece of DNA, the conformation changes and fluorescence can be detected. In this way, the amplification process can be monitored in real-time, the intensity of fluorescence corresponding directly to the level of amplification.

TaqMan™ analysis may be useful for example, for detecting the presence of the CE43-67B event in a background of wild type cotton, or for detecting the adventitious presence of CE43-67B in other germplasm. Further embodiments of the present invention include, but are not limited to, RACE PCR.

A further embodiment of the present invention involves the use of multiplex PCR for distinguishing between homozygous CE43-67B plant material and heterozygous CE43-67B plant material. This is known to those skilled in the art as zygosity testing, and involves the use of three PCR primers which bind to specific parts of the cotton genome and/or inserted DNA. The presence or absence of each of two amplification products of particular sizes indicates whether the test sample is hemizygous or homozygous for CE43-67B. Suitable primers for use in such a zygosity test are depicted as SEQ ID NOs 5, 6 and 8. Alternative suitable primers for use in such a zygosity test are depicted as SEQ ID NOs 10, 11 and 12. Zygosity tests can also be designed using primers labelled with different fluorescent probes so that the fluorescence colour of the amplification products indicates whether the test sample is hemizygous or homozygous for CE43-67B.

The present invention further provides a method for detecting a plant which contains the polynucleotide depicted as SEQ ID NO: 1 said method comprising: (a) preparing a sample containing the genomic DNA of the plant to be tested; (b) obtaining a pair of primers which are suitable for use in an amplification reaction to amplify a sequence comprising at least 18 contiguous nucleotides of the sequence depicted as SEQ ID NO: 3 and the complement thereof; (c) adding said pair of primers to said sample and the means for performing an amplification reaction; (d) performing an amplification reaction; and (e) visualising the thus amplified sequence.

The present invention further provides a method as described above wherein said primers are suitable for use in an amplification reaction to amplify a sequence comprising at least 20 contiguous nucleotides of the sequence depicted as SEQ ID NO: 3 and the complement thereof. In a still further embodiment said primers are suitable for use in an amplification reaction to amplify a sequence comprising at least 25 contiguous nucleotides of the sequence depicted as SEQ ID NO: 3 and the complement thereof. In a still further embodiment said primers are suitable for use in an amplification reaction to amplify a sequence comprising the sequence depicted as SEQ ID NO: 3 and the complement thereof.

The present invention still further provides a method as described above wherein the sequence to be amplified by said amplification reaction comprises a sequence containing the nucleotide junction of genomic sequence-transgene cassette insert (g-g) provided as nucleotides 275/276 of SEQ ID NO: 1. The person skilled in the art will appreciate that this junction can be used to characterise and thus identify the event and so it is well within the ambit of said skilled person to design and produce oligonucleotide primer sequences that are suitable for use in an amplification reaction to amplify the sequence which comprises the aforesaid junction. The person skilled in the art will also appreciate that the primer sequences suitable for use in an amplification reaction may be designed based on the genomic sequence which is 5' i.e. upstream of nucleotide number 1 of SEQ ID NO: 1 and the insert or genomic sequence which is 3' i.e. downstream of nucleotide number 545 of SEQ ID NO: 1.

The present invention further provides a method for detecting a plant which contains the polynucleotide depicted as SEQ ID NO: 1 said method comprising: (a) preparing a sample containing the genomic DNA of the plant to be tested; (b) obtaining a pair of primers which are suitable for use in an amplification reaction to amplify a sequence comprising at least 35 contiguous nucleotides of the sequence depicted as nucleotides 246 to 305 of SEQ ID NO: 1 and the complement thereof; (c) adding said pair of primers to said sample and the means for performing an amplification reaction; (d) performing an amplification reaction; and (e) visualising the thus amplified sequence. In a further embodiment said primers are suitable for use in an amplification reaction to amplify a sequence comprising at least 40 contiguous nucleotides of the sequence depicted as nucleotides 246 to 305 of SEQ ID NO: 1. In a further embodiment said primers are suitable for use in an amplification reaction to amplify a sequence comprising at least 50 contiguous nucleotides of the sequence depicted as nucleotides 246 to 305 of SEQ ID NO: 1. In a further embodiment said primers are suitable for use in an amplification reaction to amplify a sequence comprising the sequence depicted as nucleotides 246 to 305 of SEQ ID NO: 1.

In a still further embodiment said primers are suitable for use in an amplification reaction to amplify a sequence comprising at least 50, 100, 150, 200, 300, 400 or 500 contiguous nucleotides of SEQ ID NO: 1 said sequence containing the nucleotide junction between nucleotides 275 and 276 of SEQ ID NO: 1. The primers referred to above are suitable for use in an amplification reaction to amplify the sequences mentioned above and the complementary sequences thereof.

The present invention still further provides a sequence which is the amplification product of the method described above.

The present invention still further provides a sequence which is the complement of a sequence described above.

The present invention still further provides a method as mentioned above wherein the thus amplified product comprises a sequence as described above.

The present invention still further provides a method as described above wherein said pair of primers comprise a forward primer which comprises a sequence which when read in the 5'→3' direction is identical to a region of the sequence depicted as nucleotides 1 to 275 of SEQ ID NO: 1 and the reverse primer comprises a sequence which when read in the 5'→3' direction is identical to a region of the reverse complement of the sequence depicted as nucleotides 276 to 545 of SEQ ID NO: 1. The person skilled in the art will recognise that a number of primers suitable for use in the methods of the invention may be created based on the sequences provided herein and the complementary sequences thereto. In addition to this, as mentioned above, such primer sequences may be based on the sequence 5' and 3' (upstream and downstream) of the sequences depicted as SEQ ID NO: 1 and it is well within the capability of the skilled person to identify such 5' and 3' sequence.

In a particular embodiment of the invention said pair of primers comprise the sequences depicted as SEQ ID NO: 5 and 6. In a further embodiment of the invention said pair of primers comprise the sequences depicted as SEQ ID NO: 9 and 10. In a further embodiment of the invention said pair of primers comprise the sequences depicted as SEQ ID NO: 11 and 12.

The present invention further provides a method for detecting a plant which contains the polynucleotide depicted as SEQ ID NO: 2 said method comprising: (a) preparing a sample containing the genomic DNA of the plant to be tested; (b) obtaining a pair of primers which are suitable for use in an amplification reaction to amplify a sequence comprising at least 18 contiguous nucleotides of the sequence depicted as SEQ ID NO: 4 and the complement thereof; (c) adding said pair of primers to said sample and the means for performing an amplification reaction; (d) performing an amplification reaction; and (e) visualising the thus amplified sequence.

The present invention further provides a method as described above wherein said primers are suitable for use in an amplification reaction to amplify a sequence comprising at least 20 contiguous nucleotides of the sequence depicted as SEQ ID NO: 4 and the complement thereof. In a still further embodiment said primers are suitable for use in an amplification reaction to amplify a sequence comprising at least 25 contiguous nucleotides of the sequence depicted as SEQ ID NO: 4 and the complement thereof. In a still further embodiment said primers are suitable for use in an amplification reaction to amplify a sequence comprising the sequence depicted as SEQ ID NO: 4 and the complement thereof.

The present invention still further provides a method as described above wherein the sequence to be amplified by said amplification reaction comprises a sequence containing the nucleotide junction of transgene cassette insert-genomic sequence (t-a) provided as nucleotides 133/134 of SEQ ID NO: 2. The person skilled in the art will appreciate that this junction can be used to characterise and thus identify the event and so it is well within the ambit of said skilled person to design and produce oligonucleotide primer sequences that are suitable for use in an amplification reaction to amplify the sequence which comprises the aforesaid junction. The person skilled in the art will also appreciate that the primer sequences suitable for use in an amplification reaction may be designed based on the insert or genomic sequence which is 5' i.e. upstream of nucleotide number 1 of SEQ ID NO: 2 and the genomic sequence which is 3' i.e. downstream of the genomic sequence nucleotide number 1198 of SEQ ID NO: 2.

The present invention further provides a method for detecting a plant which contains the polynucleotide depicted as SEQ ID NO: 2 said method comprising: (a) preparing a sample containing the genomic DNA of the plant to be tested; (b) obtaining a pair of primers which are suitable for use in an amplification reaction to amplify a sequence comprising at least 35 contiguous nucleotides of the sequence depicted as nucleotides 104 to 163 of SEQ ID NO: 2 and the complement thereof; (c) adding said pair of primers to said sample and the means for performing an amplification reaction; (d) performing an amplification reaction; and (e) visualising the thus amplified sequence. In a further embodiment said primers are suitable for use in an amplification reaction to amplify a sequence comprising at least 40 contiguous nucleotides of the sequence depicted as nucleotides 104 to 163 of SEQ ID NO: 2. In a further embodiment said primers are suitable for use in an amplification reaction to amplify a sequence comprising at least 50 contiguous nucleotides of the sequence depicted as nucleotides 104 to 163 of SEQ ID NO: 2. In a further embodiment said primers are suitable for use in an amplification reaction to amplify a sequence comprising the sequence depicted as nucleotides 104 to 163 of SEQ ID NO: 2.

In a still further embodiment said primers are suitable for use in an amplification reaction to amplify a sequence comprising at least 50, 100, 150, 200, 300, 400 or 500 contiguous nucleotides of SEQ ID NO: 2 said sequence containing the nucleotide junction between nucleotides 133 and 134 of SEQ ID NO: 2. The primers referred to above are suitable for use in an amplification reaction to amplify the sequences mentioned above and the complementary sequences thereof.

The present invention still further provides a sequence which is the amplification product of the method described above.

The invention further provides a sequence which is the complement of a sequence described above.

The present invention still further provides a method as mentioned above wherein the thus amplified product comprises a sequence as described above.

The present invention still further provides a method as described above wherein said pair of primers comprise a forward primer which comprises a sequence which when read in the 5'→3' direction is identical to a region of the sequence depicted as nucleotides 1 to 133 of SEQ ID NO: 2 and the reverse primer comprises a sequence which when read in the 5'→3' direction is identical to a region of the reverse complement of the sequence depicted as nucleotides 134 to 1198 of SEQ ID NO: 2. The person skilled in the art will recognise that a number of primers suitable for use in the methods of the invention may be created based on the sequences provided herein and the complementary sequences thereto. In addition to this, as mentioned above, such primer sequences may be based on the sequence 5' and 3' (upstream and downstream) of the sequences depicted as SEQ ID NO: 2 and it is well within the capability of the skilled person to identify such 5' and 3' sequence.

The present invention still further provides a method for detecting plant material derived from the CE43-67B event, said method comprising: (a) preparing a sample containing the genomic DNA of the plant to be tested; (b) obtaining a probe which is capable of hybridising to a sequence selected from the group consisting of a sequence comprising at least 18 contiguous nucleotides of the sequence depicted as SEQ ID NO: 3 and a sequence comprising at least 18 contiguous nucleotides of the sequence depicted as SEQ ID NO: 4; (c) adding at least one of the probes of step (b) to said sample under conditions which allow said probe to hybridise with a complementary nucleic acid within said sample; (d) removing substantially non-hybridised probe by washing; and (e) detecting the thus hybridised probe to identify if the sample is from the CE43-67B event.

The present invention further provides a method for detecting a plant which contains the polynucleotide depicted as SEQ ID NO: 1 said method comprising (a) preparing a sample containing the genomic DNA of the plant to be tested; (b) obtaining a probe which is capable of hybridising to a sequence comprising at least 18 contiguous nucleotides of the sequence depicted as SEQ ID NO: 3; (c) adding the probe to said sample under conditions which allow said probe to hybridise with a complementary nucleic acid within said sample; (d) removing substantially non-hybridised probe by washing; and (e) detecting the thus hybridised probe to identify if the sample contains said polynucleotide.

The present invention further provides a method for detecting a plant which contains the polynucleotide depicted as SEQ ID NO: 2 said method comprising (a) preparing a sample containing the genomic DNA of the plant to be tested; (b) obtaining a probe which is capable of hybridising to a sequence comprising at least 18 contiguous nucleotides of the sequence depicted as SEQ ID NO: 4; (c) adding the probe to said sample under conditions which allow said probe to hybridise with a complementary nucleic acid within said sample; (d) removing substantially non-hybridised probe by washing; and (e) detecting the thus hybridised probe to identify if the sample contains said polynucleotide.

In a particular embodiment of the methods described above said probe comprises at least 20 contiguous nucleotides. In a still further embodiment of said method, said probe comprises at least 50, 100, 150, 200, 300, 400 or 500 contiguous nucleotides of SEQ ID NO: 1, said probe containing the nucleotide junction between nucleotides 275 and 276 of SEQ ID NO: 1 or at least 50, 100, 150, 200, 300, 400 or 500 contiguous nucleotides of SEQ ID NO: 2, said probe containing the nucleotide junction between nucleotides 133 and 134 of SEQ ID NO: 2. In a still further embodiment of the invention, said probe may comprise a fragment of a relevant polynucleotide described within this specification. In particular, said probe may comprise a polynucleotide sequence which is capable of hybridising with a sequence which characterises the event described in the present application. In a still further embodiment of said method, said washing takes place under high stringency conditions. Said probe may be generated and labelled using techniques well known to the person skilled in the art.

The probe may be, for example, a PCR product or restriction digestion fragment. In a further embodiment, the probe as described herein may be tagged with a fluorescent, radioactive, enzymatic or other suitable label to enable hybridisation to be detected. In a still further embodiment of the present invention there is provided a method of hybridising a probe to the complementary nucleic acid within the sample under stringent conditions and detecting whether the probe has hybridised. High stringency hybridisation conditions are well known to the skilled person and comprise, for example: hybridisation at a temperature of about 65° C. in a solution containing 6×SSC, 0.01% SDS and 0.25% skimmed milk powder, followed by rinsing at the same temperature in a solution containing 0.2×SSC and 0.1% SDS. The skilled person may alternatively select the following hybridisation conditions, viz., hybridisation at a temperature of between 60° C. and 65° C. in 0.3 strength citrate buffered saline containing 0.1% SDS followed by rinsing at the same temperature with 0.3 strength citrate buffered saline containing 0.1% SDS. The person skilled in the art may also select further hybridisation conditions that are equally understood to be "high stringency" conditions. Suitable techniques for detecting plant material derived from the event described herein based on the hybridisation principle include, but are not limited to Southern Blots, Northern Blots and in-situ hybridisation. The skilled person is familiar with these techniques. Typically, they involve incubating a probe with a sample, washing to remove unbound probe, and detecting whether the probe has hybridised. Said detection method is dependent on the type of tag attached to the probe—for example, a radioactively labelled probe can be detected by exposure to and development of x-ray film. Alternatively, an enzymatically labelled probe may be detected by conversion of a substrate to effect a colour change.

In a still further aspect there is provided a method for identifying a plant comprising the CE43-67B event, said method comprising (a) preparing a sample containing the genomic DNA of the plant to be tested; (b) digesting said DNA via a restriction enzyme; (c) separating the digested DNA fragments and transferring the thus separated fragments to a membrane; (d) probing the thus bound fragments with a probe, designed as described above, which probe has be labelled to allow its visualisation; (e) removing substantially non-hybridised probe; and (f) detecting the thus hybridised probe wherein said event can be characterised by said probe hybridising to fragments having a particular size.

In a further aspect there is provided a cotton event which is capable of being identified by a method according to the invention. In a particular embodiment said method is the one according to the preceding paragraph.

The present disclosure also includes a method for detecting a plant which contains a protein capable of being encoded by a polynucleotide depicted as SEQ ID NO: 7, said method comprising: (a) preparing a protein-extract of the plant to be tested; (b) providing an antibody which is capable of binding to a Cry1Ab protein from *Bacillus thuringiensis*; (c) adding said antibody to said extract under conditions which allow said antibody to bind to said protein within said extract: and (d) detecting the thus bound antibody to identify if the extract contains said protein.

The present disclosure also includes a method for detecting a plant which comprises a Cry1Ab gene from *Bacillus* thuringiensis said method comprising: (a) preparing a protein-extract of the plant to be tested; (b) providing an antibody which is capable of binding to a Cry1Ab protein from *Bacillus thuringiensis*; (c) adding said antibody to said extract or said extract to said antibody under conditions which allow said antibody to bind to said Cry1Ab protein within said extract; and (d) detecting the thus bound antibody to identify if the extract contains said Cry1Ab protein. This method is useful for distinguishing between plants expressing Cry1Ab, such as plants comprising CE43-67B, and plants not-expressing Cry1Ab.

Suitable methods of detecting plant material derived from the event described herein which methods are based on said antibody binding include, but are not limited to Western Blots, Enzyme-Linked ImmunoSorbent Assays (ELISA) and SELDI mass spectrometry. The skilled person is familiar with these and further immunological techniques. Typical steps include incubating a sample with an antibody that binds to the said protein, washing to remove unbound antibody, and detecting whether the antibody has bound. Many such detection methods are based on enzymatic reactions—for example the antibody may be tagged with an enzyme such as horseradish peroxidase, and on application of a suitable substrate, a colour change detected. Suitable antibodies may be monoclonal or polyclonal.

The present disclosure also includes a method of detecting plant material derived from an event described herein said method comprising obtaining a sample for analysis; making a protein extract of the sample; providing a test strip or dipstick designed to detect the presence of a said protein present within the sample; incubating the test strip or dipstick with the sample; and detecting whether said protein is present.

This method may be an antibody-based detection method for the events referred to herein and uses test strips or dipsticks. Typical steps include incubating a test strip or dipstick with a sample and observing the presence or absence of coloured bands on the test strip or dipstick. The coloured bands are indicative of the presence of a protein in the sample.

Such test strip or dipstick tests are usually protein specific, and may be used for rapid testing of samples in the field.

In one embodiment, the immunological method or dipstick utilises an antibody or antibodies, or fragment/fragments thereof, specific for the Cry1Ab gene from *Bacillus thuringiensis* as encoded by SEQ ID NO: 7. Antibody fragments include, but are not limited to, Fab, modified Fab, diFab, Fab', F(ab')2 or FV fragment, immunoglobulin light chain or heavy chain monomer, single chain FV (scFV) or nanobody. The antibody or fragment thereof may be monoclonal or polyclonal. In a particular embodiment, the antibody is an antibody secreted by cell lines selected from the group consisting of DSM ACC2723 and DSM ACC2724 (both deposited on 12 May 2005 at Deutsche Sammlung von Mikroorganismen and Zellkulturen GmbH, Mascheroder Weg 1b, 38124 Braunschweig, Germany) or an antibody which is capable of inhibiting the binding to the Cry1Ab of an antibody secreted by cell lines selected from the group consisting of DSM ACC2723 and DSM ACC2724. It is noted that methods for producing both monoclonal and polyclonal antibodies and fragments thereof are well known in the art.

Suitable test strips or dipsticks and materials for their use are described in PCT application WO 02/27322 and are, for example, lateral-flow immunostrips comprising a detection membrane of cellulose acetate, cellulose, nitrocellulose or nylon, supported on a plastic backing. Such an immunostrip may be produced using membranes and filters through which a liquid sample is drawn by capillary action. The protein in the sample reacts with the antibodies contained in the immunostrip as it moves the length of the strip and is captured at a line that becomes visible. Suitable means of detection are, for example, colloidal gold and coloured latex beads:

In a particular embodiment, a line of specific anti-Cry1Ab antibody, as described above, is sprayed on a test strip, which is suitably made from nitrocellulose supported on a plastic backing. A reagent control line of anti-mouse antibody is sprayed in parallel above the first antibody line. The membrane is flanked on the top by an absorption pad and on the bottom by a pad containing dried colloidal gold labelled anti-Cry1Ab antibody. In a preferred embodiment, the colloidal gold-labelled anti-Cry1Ab antibody is different from the first antibody sprayed as the test tine. In a particular embodiment, the colloidal gold-labelled anti-Cry1Ab antibody is the antibody secreted by cell line DSM ACC2723 and the antibody sprayed at the test line is the antibody secreted by cell line DSM ACC2724. A sample application pad flanks the colloidal gold pad. In use, the sample application pad is placed in a sample of extracted tissue or this sample is applied to the pad in another way, for example, by pipette. Any Cry1Ab protein contained within the sample flows up the strip and becomes bound by the colloidal gold labelled-anti-Cry1Ab antibody. As it continues up the strip, the protein also becomes bound by the anti-Cry1Ab antibody at the test line. Excess gold conjugate is captured at the reagent control line. In a positive test, that is, if Cry1Ab is present in the sample, a double red line appears: the lower line indicates the presence of Cry1Ab while the upper line is the control line signalling a properly working device.

In a still further aspect of the invention there is provided a kit of parts which comprises a pair of primers as described above and instructions for performing the method as described above and means for performing an amplification reaction and optionally means for preparing the sample to be tested. In a still further embodiment there is provided a kit of parts which comprises an antibody as described above and instructions for performing the method as described above and means for performing the method as described above and optionally means for preparing the sample to be tested. In a still further embodiment of the present invention, said kit of parts may comprise DNA amplification-detection technology such as PCR or TaqMan™. In a still further embodiment of the present invention, said kit of parts may comprise probe hybridisation-detection technology such as Southern Blots, Northern Blots or in-situ Hybridisation. In another embodiment of the present invention, said kit of parts may comprise antibody binding-detection technology such as Western Blots, ELISA's, SELDI mass spectrometry, test strips or dipsticks. In a further embodiment of the present invention, said kit of parts may comprise any combination of the aforementioned detection technologies. In a still further embodiment, said kit of parts may comprise in the form of instructions one or more of the methods described above.

In a still further aspect there is provided a plant or seed according to the invention which is used in a method of breeding. For example, the plants may be used to transfer the trait which provides for insect resistance into a plant of the same genus but having a different background germplasm. Such breeding into a different germplasm may be desired if the plant is to be grown in under conditions where an alternative germplasm is favourable. Methods for breeding that can be used to transfer the trait into a different background germplasm are well known in the art.

In a still further aspect there is provided the use of a plant or seed according to the invention to generate explant material for use in a method of transformation of said explant with a further genetic trait. Once provided with the events that can be identified by the methods of the present invention it is well within the capabilities of the person skilled in the art to generate such explant material and use in further transformation procedures. Furthermore, once provided with the events that can be identified by the methods of the present invention it is well within the capabilities of the person skilled in the art to use said events in breeding methods as described herein.

According to the present invention, there is provided the use of one or more of the polynucleotides of the invention as described above for detecting the CE43-67B event. In one embodiment, said polynucleotides may be used in a method for detecting the CE43-67B event as described above.

EXAMPLES

The invention will be further apparent from the following non-limiting examples in conjunction with the associated sequence listings as described below:

| | |
|---|---|
| SEQ ID NO 1: | CE43-67B event: Genomic sequence-Insert |
| SEQ ID NO 2: | CE43-67B event: Insert-Genomic sequence |
| SEQ ID NO 3: | CE43-67B event: Genomic sequence-Insert junction |
| SEQ ID NO 4: | CE43-67B event: Insert-Genomic sequence junction |
| SEQ ID NOs 5-6: | CE43-67B event: Primers |
| SEQ ID NO 7: | CE43-67B event: Cry 1 Ab gene sequence |
| SEQ ID NOs 8-19: | CE43-67B event: Primers |

Example 1

Cloning and Transformation 1.1 Vector Cloning

Standard gene cloning techniques of restriction digestion and ligation of fragments from in-house vectors were used to construct the transformation vectors, pNOV1914 and pNOV4641. Vector pNOV1914 included a selectable marker cassette comprising a Ubiquitin (UBQ3) promoter, the UBQ3 intron, a gene sequence which encodes a protein conferring resistance to hygromycin, and a nos polyadenylation sequence. Vector pNOV4641 included the expression cassette of the target gene, which cassette comprised a Actin (ACT2) promoter, the ACT2 intron, a sequence encoding the Cry1Ab gene that had been codon optimised for expression in maize, and a nos polyadenylation sequence.

The vectors were transformed into *Agrobacterium tumefaciens* strain GV3101 using standard *Agrobacterium* transformation techniques, and transformed cells selected via antibiotic resistance.

1.2 Plant Transformation

The CE43-67B event was produced by *Agrobacterium*-mediated transformation of *Gossypium hirsutum* L. cv Coker 312.

Coker 312 seeds were sown in the glasshouse. Tender petioles were cut from 3 to 5 weeks old plants, and sterilized by immersion in 70% ethanol. The petioles were then immersed in a 5% Clorox+2 ml/l Tween20 solution for 20 minutes. Petioles were washed 3 times in $ddH_2O$. The ends of petioles were cut off, and petioles transferred to petiole preculture medium (4.3 g/l MS salts, B5 vitamins (100 mg/l myo-Inositol, 1 mg/l nicotinic acid, 1 mg/l pyridoxine HCl, 10 mg/l thiamine HCl), 30 g/l glucose, 2.4 g/l phytogel, pH 7.0) and allowed to pre-culture in the light at 30° C. for 3 days.

2 ml cultures of *Agrobacterium* containing the pNOV1914 and pNOV4641 constructs were grown overnight in appropriate antibiotics and then diluted with liquid MMS1 medium (4.3 g/l MS salts, B5 vitamins (100 mg/l myo-Inositol, 1 mg/l nicotinic acid, 1 mg/l pyridoxine HCl, 10 mg/l thiamine HCl), 0.05 mg/l 2.4-D, 0.1 mg/l kinetin, 30 g/l glucose, pH 6.5) to an $OD_{660}$ of between 0.1 and 0.2.

The ends were cut off the petioles and placed in 10 to 20 ml of bacterial solution in a sterile petri dish. Once in the solution, the petioles were cut lengthwise and then cut into 2 cm sections. After the petiole explants had soaked in bacterial solution for 5 to 10 minutes, they were transferred to co-culture plates (same recipe as MMS1 liquid with the addition of 2.4 g/l Phytagel) overlaid with sterile filter papers, and allowed to co-culture at 24° C. for 48 to 72 hours under low light intensity. Co-cultured explants were transferred to MMS1 medium (recipe as for MMS1 liquid medium, additionally with 2.4 g/l phytogel) containing 500 mg/l cefotaxime and 10 mg/l hygromycin, and incubated at 30° C. under a light cycle of 16 hours light and 8 hours dark. Explants were transferred to fresh medium after 2 weeks, and every 4 to 6 weeks thereafter until callus was formed.

Once calli were the size of a garden pea, they were removed from the explants and transferred to fresh MMS1 medium containing 500 mg/l cefotaxime and 10 mg/l hygromycin, and maintained in tissue culture by subculturing every 4 weeks as appropriate.

1.5 g callus tissue was broken up thoroughly and placed in a 50 ml Erlenmeyer flask containing 10 ml of liquid MMS2 medium (4.3 g/l MS salts, B5 vitamins (100 mg/l myo-Inositol, 1 mg/l nicotinic acid, 1 mg/l pyridoxine HCl, 10 mg/l thiamine HCl), 1.9 g/l $KNO_3$, 30 g/l glucose, pH 6.5). The suspended callus was shaken at 100 rpm in the light at 30° C. for two weeks. The suspension culture cells were rinsed 3 times in MMS2 liquid medium, resuspended and plated onto solid MMS2 medium (recipe as per liquid MMS2 medium, additionally with 2.4 g/L phytogel). Once plated, excess liquid MMS2 medium was removed, and the plates incubated at 30° C. in the light. Plates were checked for somatic embryo development each week. Somatic embryos formed within 1 to 2 months. This step of liquid suspension could be repeated multiple times until embryogenic callus or somatic embryos were formed.

Somatic embryos were transferred to EG (embryoid germimation) medium (2.65 g/l MS salts modification No. 4 (Duchefa), 1.9 g/l $KNO_3$, B5 vitamins (as before), 30 g/l glucose, 1 g/l glutamine and 0.5 g/l asparagine, pH 6.5), and sub-cultured to fresh EG medium every 3 to 4 weeks.

Once somatic embryos turned green and were larger than 2 cm, they were plated root down in EG medium. At all stages of regeneration, growing plantlets were prevented from reaching the lids or sides of their containers to prevent leaf drop. Germinated embryos with 1 to 2 true leaves were transferred to EG medium in 175 ml Greiner containers. Strong plantlets with true leaves were transferred to sterile peat plugs expanded with $dH_2O$ in 175 ml Greiners and transferred to peat in 3 inch pots. Plants were acclimatised in a plant propagator at high humidity in a growth cabinet under conditions of 14 hours daylight at 30° C. and 10 hours darkness at 20° C. Once roots were seen growing through the drainage holes of the pot they were transferred to larger pots containing 50% John Innes No. 3 and 50% peat supplemented with Osmocote, and placed in the glasshouse.

1.3 Identification and Selection of Transgenics

Putative transgenic plants were screened by PCR for the presence of the Cry1Ab gene. Positive events were identified and screened using insect bioassays for insecticidal activity. Molecular characterisation of insecticidal lines was carried out by Southern Blot analysis. T1 seed from several events were observed in a field trial for insect resistance and agronomic quality. The CE43-67B event was chosen based on molecular characterisation, protein expression levels as identified by ELISA, insecticidal activity against *Heliothis virescens* and *Spodoptera littoralis* and field performance. The hygromycin selectable marker cassette was segregated away using conventional plant breeding to result in the CE43-67B event.

1.4 Verification of Sequence of CE43-67B

Genomic DNA was isolated from the CE43-67B event. This was used in the sequencing of the junctions of the DNA insertion site with the cotton genomic DNA in the CE43-67B event (SEQ ID NOs: 1 and 2), using standard DNA sequencing techniques.

Example 2

CE43-67B Event Specific Detection Via PCR 2.1 DNA Extraction

DNA was extracted from leaf tissue using the Wizard™ Magnetic 96 DNA Plant System (Promega, #FF3760), according to the manufacturers instructions, with an additional step at the beginning of the protocol: following grinding of the leaf material, 0.9 ml Cotton Extraction Buffer (0.2M Tris pH 8.0, 50 mM EDTA, 0.25M NaCl, 0.1% v/v 2-mercaptoethanol, 2.5% w/v polyvinyl-pyrrolidone) was added to each well, the plant tissue resuspended and the plate centrifuged at 4,000 rpm (2755 g) for 10 minutes. After aspirating and discarding the supernatant, 300 ul Lysis Buffer A (Promega) was added and the manufacturers protocol was followed from this point. This procedure resulted in approximately 85 ul of purified genomic DNA at a concentration of approximately 10 ng/ul.

2.2 Event-Specific PCR Reactions 25 ul PCR reactions were setup using a standard reaction mix comprising:

1× Jumpstart RED TaqPCR (Sigma, #P-1107)
0.5 uM primer 1 (SEQ ID NO: 9)
0.5 uM primer 2 (SEQ ID NO: 10)
10 ng genomic DNA
dd$H_2O$ The PCR reactions were heated in a thermocycler at 94° C. for 3 minutes, followed by 35 cycles as follows: 94° C. for 30 seconds, 60° C. for 30 seconds, 72° C. for 50 seconds. The reaction was completed by heating at 72° C. for 5 minutes.

PCR reactions were run on an agarose gel, and DNA bands visualised under UV light after staining with ethidium bromide. A band of 760 bp in size was obtained.

Alternatively, 25 ul PCR reactions were setup using a standard reaction mix comprising:

1× Jumpstart RED TaqPCR (Sigma, #P-1107)
0.5 uM primer 1 (SEQ ID NO: 11)
0.5 uM primer 2 (SEQ ID NO: 12)
10 ng genomic DNA
dd$H_2O$ The PCR reactions were heated in a thermocycler at 94° C. for 5 minutes, followed by 35 cycles as follows: 94° C. for 30 seconds, 60° C. for 30 seconds, 72° C. for 30 seconds. The reaction was completed by heating at 72° C. for 5 minutes.

PCR reactions were run on an agarose gel, and DNA bands visualised under UV light after staining with ethidium bromide. A band of 267 bp in size was obtained.

Example 3

CE43-67B Detection Via Multiplex PCR Zygosity Test 3.1 Genomic DNA Extraction Genomic DNA from CE43-67B was extracted as described in Example 2.1.

3.2 Multiplex PCR

PCR primers for use in a multiplex PCR zygosity test were designed. A 20 ul PCR reaction was set up for each sample to be tested as follows:

1× JumpState ReadyMix REDTaq PCR (Sigma P-1107)
0.5 uM primer 1 (SEQ ID NO: 5)
0.5 uM primer 2 (SEQ ID NO: 6)
0.5 uM primer 3 (SEQ ID NO: 8)
10 ng genomic DNA
dd$H_2O$ The PCR reactions were heated in a thermocycler at 94° C. for 3 minutes, followed by 35 cycles as follows: 94° C. for 15 seconds, 55° C. for 15 seconds, 72° C. for 45 seconds. The reaction was completed by heating at 72° C. for 5 minutes.

PCR reactions were run on an agarose gel, and DNA bands visualised under UV light after staining with ethidium bromide. The presence of 2 bands (561 bp and approximately 1000 bp) indicated that the sample was from a CE43-67B heterozygote plant; 1 band of 561 bp in size indicated that the sample was from a CE43-67B homozygote plant; and 1 band of approximately 1000 bp in size indicated that the sample was from a homozygote wild type cotton plant.

3.3 Multiplex PCR II

PCR primers for use in a multiplex PCR zygosity test were designed. A 20 ul PCR reaction was set up for each sample to be tested as follows.

1× JumpStart ReadyMix REDTaq PCR (Sigma P-1107)
0.5 uM primer 1 (SEQ ID NO: 11)
0.5 uM primer 2 (SEQ ID NO: 12)
0.5 uM primer 3 (SEQ ID NO: 13)
10 ng genomic DNA
dd$H_2O$ The PCR reactions were heated in a thermocycler at 94° C. for 3 minutes, followed by 35 cycles as follows: 94° C. for 30 seconds, 60° C. for 30 seconds, 72° C. for 45 seconds. The reaction was completed by heating at 72° C. for 5 minutes.

PCR reactions were run on an agarose gel, and DNA bands visualised under UV light after staining with ethidium bromide. The presence of 2 bands (267 bp and approximately 1000 bp) indicated that the sample was from a CE43-67B heterozygote plant; 1 band of 267 bp in size indicated that the sample was from a CE43-67B homozygote plant; and 1 band of approximately 1000 bp in size indicated that the sample was from a homozygote wild type cotton plant.

Example 4

CE43-67B Detection Via Southern Blot 4.1 DNA Extraction for Use in Southern Blotting Approximately 2 to 3 g fresh weight of frozen young leaf tissue was ground in a chilled mortar and pestle to a fine powder and added to 15 ml of ice-cold Nuclei extraction buffer (0.35M glucose, 0.1M Tris-HCl pH8, 50 mM $Na_2EDTA$, 2% Polyvinyl-pyrrolidone-10, 0.1% ascorbic acid, 0.2% B-mercaptoethanol) in a labelled tube. The sample was incubated on ice for 15-20 minutes. The tube was mixed gently and centrifuged at 2700 g for 20 minutes at 4° C. The supernatant was discarded and 8 ml of nuclei lysis buffer (0.14M sorbitol, 0.22M Tris-Cl pH8, 0.8M NaCl, 0.22M $Na_2EDTA$, 0.8% w/v CTAB, 1% Sarkosyl, 1% Polyvinyl-pyrrolidone-10, 0.1% ascorbic acid, 0.2% B-mercaptoethanol, 5 μg/ml proteinase K) was added. After mixing, the tubes were incubated at 65° C. for 30 minutes. 10 ml chloroform was added, and the tube mixed gently by inversion until an emulsion formed followed by, centrifugation at 4600 rpm for 10 minutes at room temperature.

The aqueous layer was removed into a new tube containing 10 μl RNase A (10 mg sigma R4642), and the tube incubated for 30 minutes at 37° C. The chloroform and centrifugation steps were repeated once. The aqueous layer was removed into a new tube containing 10 ml propan-2-ol. After approximately 15 minutes incubation at room temperature, a gelatinous precipitate was observed in the middle of the tube. The tube was mixed gently to precipitate out the DNA. The DNA was spooled out using a sterile loop into a falcon tube containing 70% ethanol. The DNA was air-dried to remove the ethanol and resuspended in 200-400 μl TE.

4.2 Alternative Method for DNA Extraction 2-3 young cotton leaves (approximately 1 g fresh weight) are ground to a paste in a mortar and pestle at room temperature, with 2 ml of grinding buffer (100 mM NaOAc pH 4.8, 50 mM EDTA pH8.0, 500 mM NaCl, 2% PVP (10,000 MW), 1.4% SDS) and a little sand. The ground tissue is transferred to a 15 ml falcon tube, and the remnants in the mortar rinsed with 1 ml of grinding buffer into the tube. The sample is incubated at 65° C. for 15 minutes, shaking occasionally. 4 ml 10M ammonium acetate is added, and the sample mixed well and incubated at 65° C. for 10 minutes to precipitate proteins. The samples are centrifuged at room temperature at 4600 rpm for 10 minutes. The aqueous phase is transferred to a fresh 15 ml tube.

0.6 volumes of cold isopropanol are added and the sample is incubated at room temperature for approximately 30 minutes. After mixing by slowly inverting the tube several times, the DNA is spooled out and dissolved in 500 ul TE. 10 ul of 10 mg/ml RNAse are added and incubated for 15 minutes at room temperature. Following extraction with 500 ul of phenol: chloroform: isoamyl alcohol (25:24:1), the sample is mixed gently and centrifuged at 13000 rpm for 5 min.

The supernatant is transferred to a fresh tube using a fine Pasteur pipette and re-extracted with chloroform: isoamyl alcohol (24:1) as above. The supernatant is transferred to fresh tubes, 1/10 volume 3M NaOAc (pH4.8) added and mixed, and then one volume cold isopropanol is added. The sample may be incubated at room temperature for up to 30 minutes to precipitate the DNA. The DNA is spooled out and resuspended in 70% ethanol. The DNA is air-dried to remove the ethanol and resuspended in 200 ul water.

4.3 Restriction Enzyme Digests

The DNA was quantified Using a spectrophotometer and running out on a gel. Suitable enzyme digests were prepared using 5 ug DNA per digest in a total volume of 40 ul. Digests including NcoI, MscI, HindIII/KpnI and NheI/AscI were used to detect copy number and insert integrity. Digests were incubated for 6 hours at the appropriate temperature for each enzyme.

4.4 Gel Electrophoresis

Bromophenol blue loading dye was added to each sample from 4.3 above, and each sample loaded on a 0.8% TBE agarose gel. The gel was run at 50 volts overnight.

After running, the gel was washed in 0.25M HCl for 10 minutes to depurinate the DNA, incubated in denaturing solution (0.5M NaOH, 1.5M NaCl) with gentle agitation for 30 minutes, rinsed with distilled water and then incubated in neutralising solution (0.5M Tris, 1.5M NaCl) for 30 minutes.

A Southern Blot was prepared as follows: A glass plate was placed over a tray containing 20×SSC and a strip of 3M paper was placed onto the glass plate such that both ends dipped into the 20×SSC solution (to act as a wick). A piece of 3M paper the same size as the gel was placed on the wick, and the gel placed on this. Strips of nescofilm were laid around the edges of the gel to form a seal. A Hybond membrane was placed on top of the gel, followed by two further pieces of 3M paper. Throughout the assembly of the blot, care was taken to ensure that no air bubbles were trapped between the membrane, gel and 3M paper. A 5 cm-10 cm stack of absorbent paper towels was placed on top of the 3M paper and held in place with a weight.

The DNA was allowed to transfer to the Hybond membrane overnight. After transfer the Southern Blot stack was disassembled and the DNA was bound to the membrane via UV cross-linking.

4.5 Hybridisation

A suitable DNA probe was prepared by HindIII/KpnI restriction digestion of binary plasmid pNOV4641 and purification of the resulting fragment. 25 ng probe DNA in 45 ul TE was boiled for 5 minutes, placed on ice for 5 minutes then transferred to a Rediprime II (Amersham Pharmacia Biotech, #RPN 1633) tube. After addition of 5 ul 32P-labelled dCTP to the Rediprime tube, the probe was incubated at 37° C. for 1 hour. The probe was purified by centrifugation through a microspin G-50 column (Amersham Pharmacia Biotech, #27-5330-01) according to the manufacturers instructions to remove unincorporated dNTPs. The activity of the probe was measured roughly by comparing the amount of radioactive component remaining in the column to the amount in the sample tube, with a ratio of at least 50:50 being acceptable. The Hybond membrane was pre-hybridised by wetting with 40 ml pre-warmed Rapid-Hyb buffer (Amersham-Pharmacia), at 65° C. for 30 minutes. The labelled probe was boiled for 5 minutes, and placed on ice for 5 minutes. An appropriate amount of probe (1 million counts per 1 ml pre-hybridisation buffer) was added to the pre-hybridisation buffer and hybridisation occurred at 65° C. overnight. The following day, the hybridisation buffer was discarded, and following a rinse with 50 ml 2×SSC/1% SDS solution the membrane washed in 150 ml 2×SSC/1% SDS solution at 65° C. for 30-45 minutes. This process was repeated twice with 0.1×SSC/1% SDS solution. The membrane was exposed to a phosphor screen or X-ray film to detect where the probe had bound.

Example 5

CE43-67B Detection Via ELISA 5.1 Protein Extraction

Cotton tissue for analysis was harvested and frozen at −70° C. Frozen tissue was ground to a fine powder and weighed into a labelled polypropylene tube; Extraction buffer (100 mM Tris, 100 mM Sodium Borate, 5 mM MgCl, 0.05% Tween 20, 0.2% Sodium Ascorbate, Water, pH 7.8, 1 mM AEBSF, 0.001 mM Leupeptin) was added to the sample in a ratio of 2:1 (volume extraction buffer:sample fresh weight) for frozen tissue or 30:1 (volume extraction buffer: sample dry weight) for lyophilised tissue. The sample was vortexed and homogenised using a Brinkman PT 10/35 Polytron equipped with a PTA 10TS foam-reducing generator, until the mixture became liquefied. Extracts were centrifuged at 10,000×g for 15 minutes. The protein extract supernatant was stored at 2-8° C.

5.2 Elisa Protocol

The ELISA procedure used standard techniques as follows. A 96-well plate was soaked in ethanol for 2 hours, and air-dried. The plate was coated with 50 ul goat anti-Cry1Ab antibody per well and incubated overnight at 2-8° C. After washing three times with 1× ELISA wash solution (100 mM Tris, 0.5% Tween-20, 75 mM NaCl, pH8.5), the plate was dried briefly by tapping upside down on a paper towel. 150 ul blocking solution (10 mM $NaPO_4$, 140 mM NaCl, 1% BSA, 0.02% Sodium Azide, titrated to pH7.4 with $NaH_2PO_4$ and $Na_2HPO_4$) was added to each well followed by incubation at room temperature for 45 minutes. The plate was washed 3 times as described above.

Cry1Ab standards and protein extract samples were applied to appropriate wells of the plate in triplicate, 50 ul total volume per well. The plate was incubated at 2-8° C. for 1 hour 30 minutes, followed by room temperature for a further 30 minutes. The plate was washed three times with ELISA wash solution, and then incubated at 35-39° C. for 1 hour with 50 ul rabbit anti-Cry1Ab antibody per well. The plate was washed three times with ELISA wash solution, and incubated at room temperature for 30 minutes with 50 ul donkey anti-rabbit antibody conjugated with alkaline phosphatase per well. Following a further three washes with ELISA wash solution, 50 ul phosphatase substrate solution was added per well and the plate incubated for 30 minutes at room temperature. The reaction was stopped by addition of 50 ul 3M NaOH per well. The absorbance of the solution in each well was measured at 405 nm using a Ceres 900 C multiwell plate reader and the results analysed using KC3 Curve fitting software (Bio-Tek Instruments Inc.). The concentration of Cry1Ab in the samples was calculated by reference to the Cry1Ab protein standards.

Example 6

CE43-67B Detection Via Dipstick 6.1 Protein Extraction

A piece of leaf tissue approximately 0.2 $cm^2$ was placed in a tube containing extraction buffer. A plastic stirrer was used to extract protein from the tissue, by cutting into and macerating the tissue.

6.2 Dipstick Test

A test strip was placed into the tube and incubated for 5 to 10 minutes for the result to develop. The test strip comprised a first band at which anti-Cry1Ab antibody was bound, and a second band at which a control antibody was bound. After incubation, a double red line in the result window of the test strip indicated that Cry1Ab was present. The lower line indicated the presence of Cry1Ab protein while the upper line was a control indicating that the assay was working correctly.

Example 7

CE43-67B Detection Via End-Point Taqman Zygosity Test 7.1 Genomic DNA Extraction Genomic DNA from CE43-67B was extracted as described in Example 2.1.

7.2 End-point TaqMan PCR

PCR primers for use in a end-point TaqMan PCR zygosity test were designed. A 20 ul PCR reaction was set up for each sample to be tested as follows:

1× JumpStart ReadyMix REDTaq PCR (Sigma P-1107)
0.5 uM primer mix 1 (equimolar concentrations of SEQ ID NOs: 14, 15 and 16)
0.5 uM primer mix 2 (equimolar concentrations of SEQ ID NOs: 17, 18, and 19)
10 ng genomic DNA
dd$H_2O$ The PCR reactions were heated in a thermocycler at 95° C. for 5 minutes, followed by 40 cycles as follows: 95° C. for 15 seconds, 60° C. for 1 minute.

7.3 Analysis

Fluorescence values were read on the ABI 7900HT, and the end-point analysis run using the Allelic Discrimination program in the SDS software provided. Detection of FAM fluorescence indicated that the sample was from a CE43-67B homozygote plant. Detection of TET fluorescence indicated that the sample was from a homozygote wild type cotton plant. Detection of FAM and TET fluorescence indicated that the sample was from a CE43-67B heterozygote plant.

Example 8

Insecticidal Efficacy of CE43-67B 8.1 Field Trial I—Design

Field trials were set up at 6 locations in the US to test the insect resistance of CE43-67B. At each location, duplicate trials were planted in a randomized complete block design, each comprising 4 replicates. Each trial consisted of a plot comprising 4×40 ft rows, planted at 3 plants per foot.

At each location, one trial was artificially infested with *Heliothis virescens* (tobacco budworm) larvae, and the other with *Helicoverpa zea* (cotton bollworm) larvae when the plants were actively squaring. The trials were subsequently assessed for percentage damage to bolls and squares. The artificial infestations were carried out by spraying eggs in a solution of xanthan gum onto the plants so that the neonate larvae hatched directly onto the plants. Infestations were designed to give approximately 3 eggs per plant.

8.2 Field Trial I—Results

The data presented in the table below are the mean of all assessments taken during the trials: multiple square damage and boll damage ratings have been averaged together to give a mean fruiting body damage rating, and data from all 6 locations has been averaged together.

| | % damaged fruiting bodies (average of squares and bolls, over 6 trial locations) | |
|---|---|---|
| | *Heliothis virescens* | *Helicoverpa zea* |
| Coker312 | 28.31 | 39.35 |
| CE43-67B | 1.60 | 2.67 |

The data clearly show that CE43-67B has excellent resistance to both *Heliothis virescens* and *Helicoverpa zea* when compared to the non-transgenic control designated Coker312.

8.3 Field Trial II—Design

CE43-67B plants were artificially infested with tobacco budworm (*Heliothis virescens*) eggs, which were obtained from the Southern Insect Management Laboratory in Stoneville, Miss. 24 to 36 hours prior to artificial infestation. Eggs were mixed into a xanthan gum solution and sprayed onto the terminal area of the cotton plants utilizing a conventional $CO_2$ backpack sprayer. Eggs were sprayed through a flat fan 8006 nozzle at approximately 10 psi. The trial was carried out at 2 locations, Syngenta's Southern Regional Technical Centre at Leland, Miss. and Vero Beach Research Centre at Vero Beach, Fla. At both locations, unreplicated, solid blocks of approximately 2240 plants of CE43-67B, as well as smaller blocks of approximately 224 plants of non-transgenic Coker 312 were utilized for the infestation. If populations of natural enemies were deemed to be sufficiently high to interfere with infestation, the study area was over sprayed with acephate (Orthene®) at 0.5 lb ai/A 24 to 48 hours before scheduled infestation. The non-transgenic Coker 312 cotton block was used to estimate the infestation technique effectiveness and to determine field fitness of the tobacco budworm strain utilized in these studies. At each location, four artificial infestations were made to CE43-67B and Coker 312 cotton with one quarter of the available plants being infested each time. The infestations were carried out between mid-squaring and early bloom. Egg hatch rate was estimated by collecting several leaves containing eggs from Coker 312 plants and placing them into Petri dishes. Eggs on the collected leaves were counted and two to three days later, successful larval eclosion was assessed. Assessments were carried out 7 days after infestation. One half of all infested plants were assessed at the Leland, Miss. location, whereas three quarters of all infested plants were assessed at the Vero Beach, Fla. location. In each case, the assessment involved a thorough whole plant search for surviving larvae. Square damage ratings were also taken from the Leland trial. Where surviving larvae were found on CE43-67B plants, the fruiting structures containing the larva were tagged. Four to 7 days later, these fruiting structures, plus all adjacent structures were thoroughly assessed again to evaluate whether the larvae were still surviving. Similar later assessments were not carried out on the Coker 312 plots because by this stage many of the larvae that had been on these plants had begun to search for pupation sites in the soil.

8.4 Field Trial II—Results

The table below is a summary of the data collected.

| Location: | Leland, MS | | Vero Beach, FL | |
|---|---|---|---|---|
| Genotype: | Coker 312 | CE43-67B | Coker 312 | CE43-67B |
| No. plants infested | 112 | 1120 | 168 | 1680 |
| No. larvae infested* | 3080 | 30800 | 5208 | 52080 |
| No. larvae recovered 7 days after infestation | 314 | 1 | 141 | 2 |
| No. larvae recovered 10-14 days after infestation | ND | 0 | ND | 0 |
| No. squares assessed | 2760 | 26825 | ND | ND |
| % squares damaged | 28 | 1 | ND | ND |

*Estimated based on the number of eggs applied and the observed hatch rate
ND = not determined The larvae surviving on CE43-67B plants 7 days after infestation at both locations were very small, ranging from the first to third instar. The fruiting structures that contained live larvae 7 days after infestation were tagged and assessed again 4 to 7 days later. At the second assessment, no live larvae could be recovered in the tagged, or surrounding fruiting structures. Furthermore, all the tagged fruiting structures remained on the plants and were developing normally. This strongly suggests that the few small larvae that were still alive on CE43-67B plants 7 post after infestation did not survive to the second assessment.

The levels of square damage observed on CE43-67B plants were extremely low in comparison to the non-transgenic Coker 312 control, confirming that the tobacco budworm larvae were vigorous and capable of establishing a robust infestation.

The data from this artificial infestation trial show that CE43-67B has excellent resistance to tobacco budworm when compared to the non-transgenic control designated Coker 312.

What is claimed is:

1. A method for detecting a plant which contains the polynucleotide depicted as SEQ ID NO: 1, said method comprising:

a) preparing a sample containing the genomic DNA of the plant to be tested;

b) obtaining a pair of primers that, when used in a nucleic acid amplification reaction with genomic DNA from cotton event CE43-67B produce an amplicon comprising at least 18 contiguous nucleotides of the sequence depicted as SEQ ID NO: 3 and the complement thereof;

c) adding said pair of primers to said sample and the means for performing an amplification reaction;

d) performing an amplification reaction; and e) detecting the thus amplified sequence.

2. The method according to claim 1, wherein said amplified sequence comprises at least 20 contiguous nucleotides.

3. The method of claim 1, wherein the pair of primers comprise a first primer sequence which is or is complementary to a cotton plant genome flanking the point of insertion of a heterologous DNA sequence inserted into the cotton plant genome of cotton event CE43-678, and a second primer sequence which is or is complementary to the heterologous DNA sequence inserted into the cotton plant genome of the cotton event CE43-67B.

4. The method of claim 3, wherein the first primer sequence comprises a sequence selected from the group consisting of SEQ ID NO: 5, SEQ ID NO: 11, SEQ ID NO: 17, and SEQ ID NO: 19; and wherein the second primer sequence comprises a sequence selected from the group consisting of SEQ ID NO: 6 and SEQ ID NO: 12.

5. The method of claim 4, wherein the first primer sequence comprises SEQ ID NO: 5 and the second primer sequence comprises SEQ ID NO: 6.

6. The method of claim 4, wherein the first primer sequence comprises SEQ ID NO: 11 and the second primer sequence comprises SEQ ID NO: 12.

7. A method for detecting a plant which contains the polynucleotide depicted as SEQ ID NO: 2, said method comprising:

a) preparing a sample containing the genomic DNA of the plant to be tested;

b) obtaining a pair of primers that, when used in a nucleic acid amplification reaction with genomic DNA from cotton event CE43-67B produce an amplicon comprising at least 18 contiguous nucleotides of the sequence depicted as SEQ ID NO: 4 and the complement thereof;

c) adding said pair of primers to said sample and the means for performing an amplification reaction;

d) performing an amplification reaction; and e) detecting the thus amplified sequence.

8. The method according to claim 7, wherein said sequence comprises at least 20 contiguous nucleotides.

9. The method of claim 7, wherein the pair of primers comprise a first primer sequence which is or is complementary to a cotton plant genome flanking the point of insertion of a heterologous DNA sequence inserted into the cotton plant genome of cotton event CE43-67 B, and a second primer sequence which is or is complementary to, the heterologous DNA sequence inserted into the cotton plant genome of the cotton event CE43-67B.

10. The method of claim 9, wherein the first primer sequence comprises a sequence selected from the group consisting of SEQ ID NO: 9 and SEQ ID NO: 15; and wherein the second primer sequence comprises a sequence selected from the group consisting of SEQ ID NO: 10, SEQ ID NO: 14, and SEQ ID NO: 16.

11. The method of claim 10, wherein the first primer sequence comprises SEQ ID NO: 9 and the second primer sequence comprises SEQ ID NO: 10.

12. A method for detecting a plant which contains the polynucleotide depicted as SEQ ID NO: 1 and/or the polynucleotide depicted as SEQ ID NO: 2 said method comprising:

a) preparing a sample containing the genomic DNA of the plant to be tested;

b) obtaining at least one probe which is capable of hybridizing to a sequence selected from the group consisting of a sequence comprising at least 1 8 contiguous nucleotides of the sequence depicted as SEQ ID NO: 3 and a sequence comprising at least 18 contiguous nucleotides of the sequence depicted as SEQ ID NO: 4;

c) adding at least one of the probes of step (b) to said sample under conditions which allow said probe to hybridize with a complementary nucleic acid within said sample;

d) removing substantially non-hybridized probe; and e) detecting the thus hybridized probe to identify if the sample contains said polynucleotide.

13. The method according to claim 12 wherein said probe comprises a sequence selected from the group consisting of SEQ ID NO: 3, SEQ ID NO: 4, and SEQ ID•NO: 15.

14. The method according to claim 12 wherein said substantially non-hybridized probe is removed by rinsing said probe under high stringency conditions.

* * * * *